(12) United States Patent
Berndt

(10) Patent No.: US 6,359,683 B1
(45) Date of Patent: Mar. 19, 2002

(54) METHOD FOR DETERMINING THE VOLUME OF PARTICLES SUSPENDED IN LIQUIDS

(75) Inventor: Klaus W. Berndt, Timonium, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/560,078

(22) Filed: Apr. 27, 2000

(51) Int. Cl.⁷ .............................................. G01N 33/48
(52) U.S. Cl. ..................... 356/39; 356/335; 356/627
(58) Field of Search ............................ 356/39, 335, 627

(56) References Cited

U.S. PATENT DOCUMENTS 3,819,270 A * 6/1974 Hirschfeld .................... 356/39
3,822,095 A * 7/1974 Hirschfeld .................... 356/39

* cited by examiner

*Primary Examiner*—Frank G. Font
*Assistant Examiner*—Roy M. Punnoose
(74) *Attorney, Agent, or Firm*—Bruce S. Weintraub

(57) ABSTRACT

The present invention relates to the field of quantitative microspectroscopy, and in particular to a method for determining the volume of particles that are suspended in liquids.

24 Claims, 4 Drawing Sheets

METHOD FOR DETERMINING THE VOLUME OF PARTICLES SUSPENDED IN LIQUIDS

FIELD OF THE INVENTION

The present invention relates to the field of quantitative microspectroscopy, and in particular to a method for determining the volume of particles that are suspended in liquids.

BACKGROUND OF THE INVENTION

In many areas of science, medicine and technology, there exists a need to determine the volume of small particles in liquids. Often, the volume of individual particles is of interest, but in other cases the relative volume content of a whole population of particles within a liquid volume has to be determined. A typical example is related to the determination of the mean volume of the red cells in blood, and to the determination of the relative volume content of the red cells in a given blood volume, which is called hematocrit.

Usually, the hematocrit is determined by centrifugating a given volume of blood, measuring the column height of the red blood cells, measuring the overall height of the centrifugated sample, and calculating the ratio of the two. The volume of single cells is most often determined by using flow cytometers or impedance counters.

All of these methods require pre-processing steps that make the test relatively labor-intensive and costly. Moreover, the instrumentation involved can be extremely expensive. Consequently, there exists a need for a simple and inexpensive method for determining the volume of single particles and for the determination of the relative volume content of a whole particle population within a given volume of liquid.

SUMMARY OF THE INVENTION

It is an objective of the present invention to provide a method for determining the volume of particles that are suspended in liquids.

According to the present invention, the above objective is achieved by depositing a liquid sample that contains suspended particles into an optical cuvette having an entrance window and an output window at a known distance from each other, by adding and evenly distributing a light-absorbing dye into the liquid sample that does not leak into the suspended particles, by sending light of such a wavelength through the cuvette that is highly absorbed by the added dye, but only weakly absorbed by the suspended particles, by measuring the optical transmission through the cuvette in an area that contains no particles, by measuring the optical transmission through the cuvette in an area that contains particles, and by calculating the volume of the suspended particles based on these transmission values and the known distance of the cuvette windows.

DETAILED DESCRIPTION OF THE INVENTION

According to the method of the present invention, a liquid sample that contains suspended particles is deposited into an optical cuvette having an entrance window and an output window at a known distance from each other. Preferably, the cuvette is relatively thin and suitable to be positioned onto the sample stage of a microscope. For example, the cuvette can be a thin cuvette having a distance between the entrance window and the output window of about 1 micron to about 3000 microns. In addition, in another embodiment, the cuvette can be a thick cuvette having a distance between the entrance window and the output window of about 1 micron to about 50 cm. A light-absorbing dye is mixed into the liquid sample. The dye selected is one that does not leak into the suspended particles. Then, light is sent through the cuvette of such a wavelength that it is highly absorbed by the added dye, but only weakly absorbed by the suspended particles.

If the liquid sample is blood and the particles are red blood cells, then, as an example, the dye TO-PRO-3, (sold, for example, by Molecular Probes, Inc., Eugene, Oreg.) can be used. In this case, the cuvette should be illuminated at a wavelength of approximately 640 nm. Light of this wavelength is highly absorbed by TO-PRO-3, but much less absorbed by red blood cells. The dye TO-PRO-3 is known for not penetrating the membrane of red blood cells.

Another possible dye would be TO-PRO-5 (sold, for example, by Molecular Probes, Inc.), which also does not penetrate into the red blood cells. In this case, the liquid sample should be illuminated with light having a wavelength of approximately 750 nm.

Figure 1:
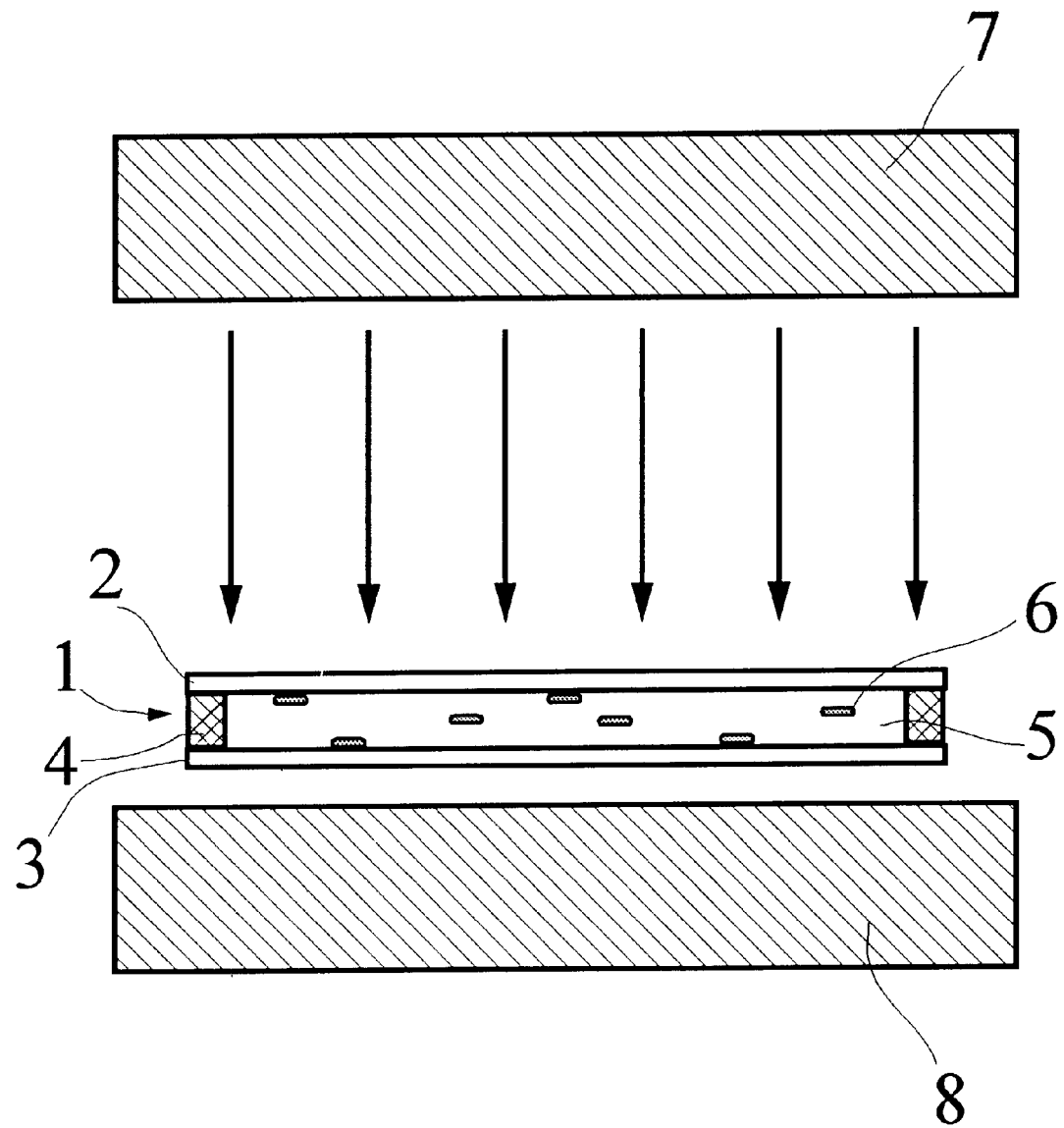
FIG. 1 depicts a measuring set-up with an optical cuvette containing a liquid sample and suspended particles.

In order to determine the volume of the suspended particles, the cuvette is placed in front of an imaging photodetector. This is illustrated in FIG. 1, where the cuvette 1 is shown having an entrance window 2 and an output window 3 that are separated by the cuvette walls 4. Cuvette 1 is filled completely with the liquid sample 5 comprising particles 6. As shown in FIG. 1, a light source 7 illuminates cuvette 1, which is positioned in front of an imaging photodetector 8. In a preferred embodiment of the invention, a charge-coupled device ("CCD") can be used as the imaging photodetector.

In order to determine the volume of the suspended particles, the following steps are performed (see FIG. 2):

First, the intensity of the input light injected into the cuvette through the entrance window ($I_0$), and the output intensity leaving the cuvette through the output window ($I_1$) are measured over an area that contains no particles. The intensity of the input light injected into the cuvette ($I_0$) can be easily measured by using a second cuvette that is filled with a non-absorbing liquid calibration sample, or by just removing the cuvette, measuring the intensity arriving at the imaging photodetector without a cuvette in place, and correcting for the reflection loss at the cuvette windows by taking into account the refractive indices involved in the sample measurement.

Second, the intensity of the input light injected into the cuvette through the entrance window ($I_0'$), and the output intensity leaving the cuvette through the output window ($I_3$) are measured over an area that contains a particle.

Third, the measured intensity values and the known distance between the entrance window and the output window ($X_0$) are combined to calculate the volume of the particle using the following equation (1):

$$V = Ax_0 \left[ 1 - \frac{lg(I_3/I_0')}{lg(I_1/I_0)} \right] \quad (1)$$

In equation (1), V is the volume of the particle, A is the area of the particle as determined by the imaging photodetector 8, $x_0$ is the distance between the entrance window and the output window, $I_0$ is the intensity injected into the area containing no particles, $I_1$ is the intensity re-emitted from the area containing no particles, $I_0'$ is the intensity injected into the area containing a particle, $I_3$ is the intensity re-emitted from the area containing a particle, and lg is logarithm.

Figure 2:
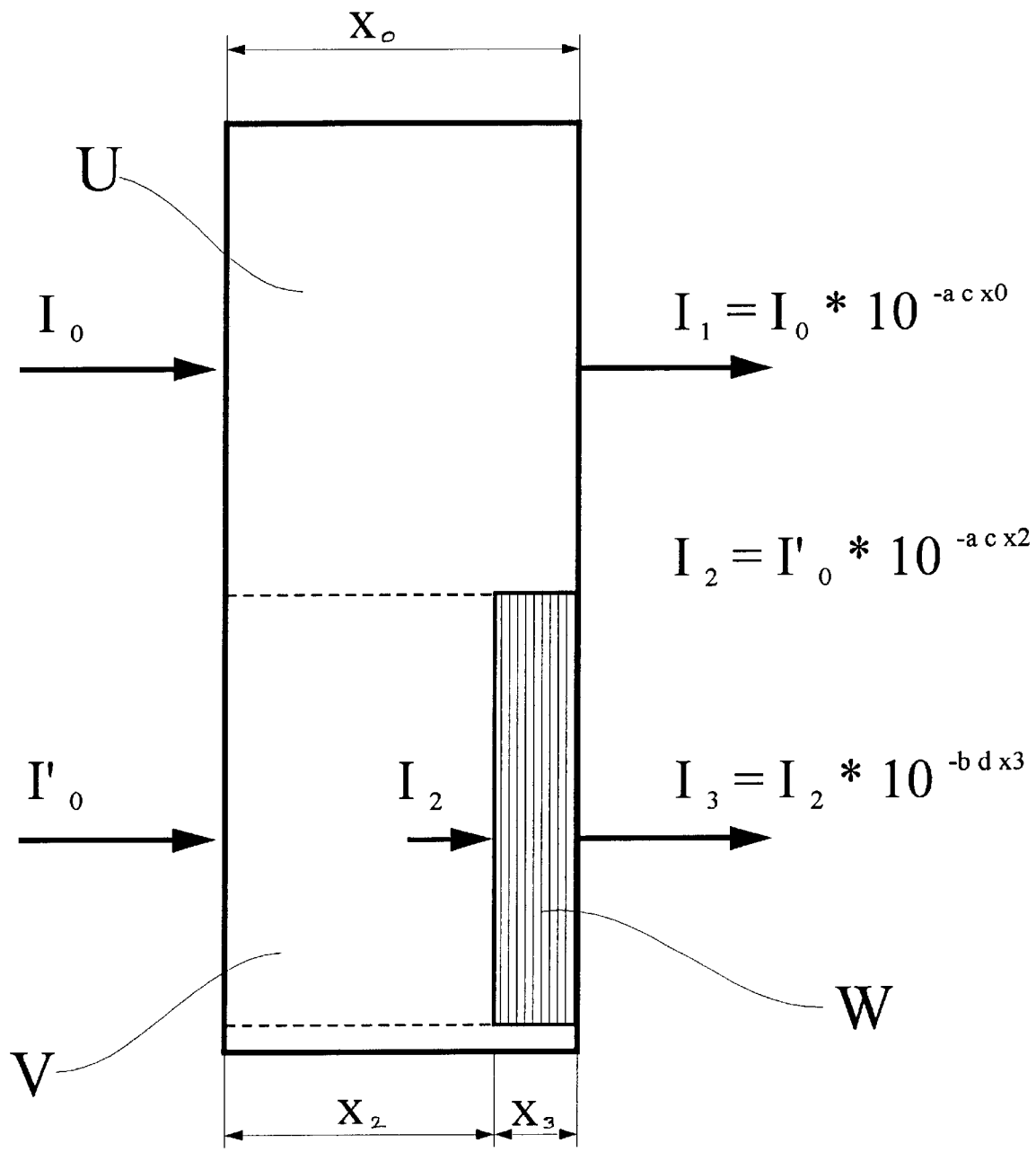
FIG. 2 shows schematically an optical cuvette with a region having no particles in it, and another region having one symbolic particle attached to the output window.

FIG. 2 shows schematically an optical cuvette with a region U having no particles in it, and another region V having one symbolic particle W attached to the output window. This figure helps to demonstrate how equation (1) has been derived.

The high absorption in the liquid without particles is characterized by the extinction coefficient, a, of the added dye; by the dye concentration, c, of the dye, and by the full distance, $x_0$, between the entrance window and the output window. The re-emitted intensity is given by equation (2):

$$I_1 = I_0 10^{-acx_0} \quad (2)$$

The absorption in the area having a particle is characterized by the particle over a distance $x_3$, with an extinction coefficient, b, and a concentration, d, and by the same dye as in area U over a distance, $x_2$, as shown in equation (3) below:

$$x_2 = x_0 - x_3 \quad (3)$$

Assuming an injected intensity, $I_0'$, the intensity, $I_3$, leaving this area is given by equation (4):

$$I_3 = I_0 10^{-(ac(x_0-x_3)+bdx_3)} \quad (b\ 4)$$

Under the condition that the absorption within the particle can be neglected, combining equations (2), (3) and (4) results in equation (1). Equation (1) shows that the quantities a, c, b, and d do not have to be determined explicitly.

If a sufficiently thin cuvette is used, the volume of single particles can be determined under the microscope. In this case, the experimental situation is still equivalent to the one illustrated in FIG. 1, except that imaging lenses are involved that are not present in FIG. 1. Using a microscope allows for high spatial lateral resolution. Therefore it is very easy to select areas that contain either no particles or that contain just a single particle (e.g., a red blood cell). By using an imaging photodetector such as a CCD camera, it is possible to determine the area A in equation (1) that is being occupied by the particle. This is done by determining all those pixels within the image that show an increased light intensity. Due to the very low absorption within the particle, light reemerging from the cuvette after passing through the particle will have a higher intensity as compared to light that is being highly absorbed over the full thickness ($x_0$) of the cuvette. Determining the number of all pixels that have a higher intensity is a well-known standard procedure of common image processing.

The principle of the present invention is not limited to single particles. If a thicker cuvette is used, then many suspended particles can build a cluster of particles. If whole blood is the sample under investigation, then many red blood cells are known to form such clusters. This aggregation phenomenon is called Roleaux. formation. In this case, the procedure according to the invention is executed as in the case of single particles. In other words, in a first step the injected and the reemerging light intensities are measured in an area that does not contain any particles. Then the injected and the reemerging light intensities are measured in an area which contains a cluster of particles. The measured light intensities and the area that is filled with particles are inserted into equation (1) which results, in this case, in the volume occupied by the cluster of particles. Due to the fact that the total volume between the entrance window and the output window can be calculated ($X_0$ is known), one can calculate the percentage of the total volume which is being occupied by particles. For whole blood, this percentage is called "hematocrit".

In a modification of the invention, the absorbing dye can be a fluorescent dye. In this case, the dye will have a very high absorption at a first wavelength, and will emit fluorescent light at a second wavelength. This will allow for additional analytical tests. The dyes TO-PRO-3 and TO-PRO-5 mentioned above are fluorescent dyes that highly absorb at 640 nm and 750 nm, and emit fluorescence light at 660 nm and 770 nm, respectively. Using fluorescent dyes instead of absorbing ones would allow one to, for example, study other particles that may be also present within the liquid sample.

Figure 3:
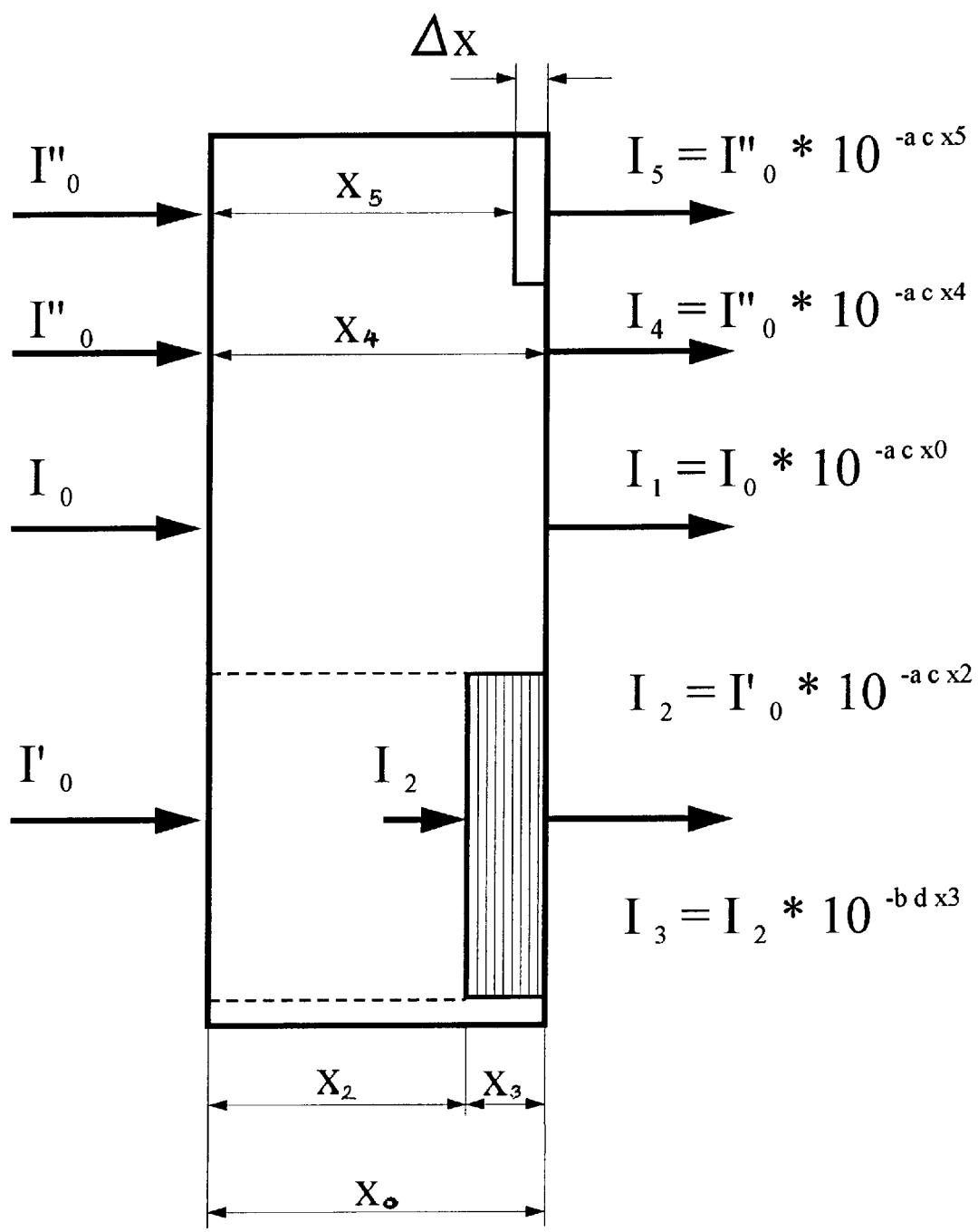
FIG. 3 shows schematically an optical cuvette according to FIG. 2 but with an additional jump ($\Delta x$) in the distance between the two cuvette windows.

Instead of knowing the total distance between the two cuvette windows ($X_0$), it is also possible to establish a well-defined jump ($\Delta x$) in this distance. This is illustrated in FIG. 3. The two corresponding output intensities in an area without particles can be used to calculate the product a*c for the absorbing dye (where a is the extinction coefficient of the added dye and c is the dye concentration of the dye) according to equation (5):

$$ac = -\frac{lg(I_4/I_5)}{\Delta_x} \quad (5)$$

where $I_4$ and $I_5$ are the intensities measured over two distances $x_4$ and $x_5$ that differ by $\Delta x$ according to equation (6):

$$\Delta x = x_4 - x_5 \quad (6)$$

In order to reduce this option to practice, one could, for instance, glue a small flat piece of glass having a thickness ($\Delta x$) onto one of the cuvette windows. In this case, the thickness of the cuvette away from the added piece of glass would be $x_4$, and the reemerging intensity $I_4$. Within the area of the added piece of glass, the cuvette thickness would be $x_5$ with $x_5 < x_4$, and the reemerging light intensity would be $I_5$. In this context, it is important to emphasize that the absolute values of $x_4$ and $x_5$ do not have to be known. Instead, only the difference $\Delta x = x_4 - x_5$, i.e., the thickness of the added piece of glass has to be known.

Equation (5) is obtained in the following way. The intensities $I_4$ and $I_5$, are given by $$I_4 = I_0'' 10^{-acx_4} \quad (7)$$

and $$I_5 = I_0'' 10^{-acx_5} \quad (8)$$

respectively, where $I_0''$ is the injected input light intensity. Dividing equation (7) by equation (8), taking the logarithm and considering that $x_4 - x_5 = \Delta x$, results, after an easy transformation, in equation (5), which is an expression for the product a*c.

Similarly, dividing equation (2) by equation (4), and taking the logarithm results in $$\lg(I_1/I_3) = \lg(I_0/I'_0) - acx_3 \qquad (9)$$

which reduces to $$\lg(I_1/I_3) = -acx_3 \qquad (10)$$

if we assume $I_0 = I_0'$ which is very reasonable. Finally, combining equations (5) and (10) results in $$x_3 = \frac{lg(I_1/I_3)}{lg(I_4/I_5)} \Delta_x \qquad (11)$$

which is an expression for the particle thickness ($x_3$) that does not contain the thickness of the cuvette anymore.

In order to calculate the particle volume, the particle thickness ($x_3$) has to be multiplied with the area (A) occupied by the particle, which finally results in $$V = A \frac{lg(I_1/I_3)}{lg(I_4/I_5)} \Delta_x \qquad (12)$$

In contrast to the method according to equation (1), the method according to equation (12) does not contain quantities representing the injected input light intensity. Due to the fact that it also does not contain the thickness of the cuvette ($x_0$), it is easier to realize and represents therefore the most preferred option of the invention.

In FIG. 2, one particle of a regular shape is present. It can be shown that the shape of the particles can be irregular and that the position of the particles within the volume has no impact on the calculated volume. The volume is related to the spatially dependent particle height, $x_3(\xi,\eta)$, via the equation (13):

$$V = \int x_3(\xi,\eta) d\xi d\eta \qquad (13)$$

In any spectrophotometric instrument, the integration is performed automatically by collecting all photons that are emitted over the area of the particle.

The following example is purely for demonstrative purposes, and is not intended to in any way limit the present invention.

EXAMPLE 1

Figure 4:
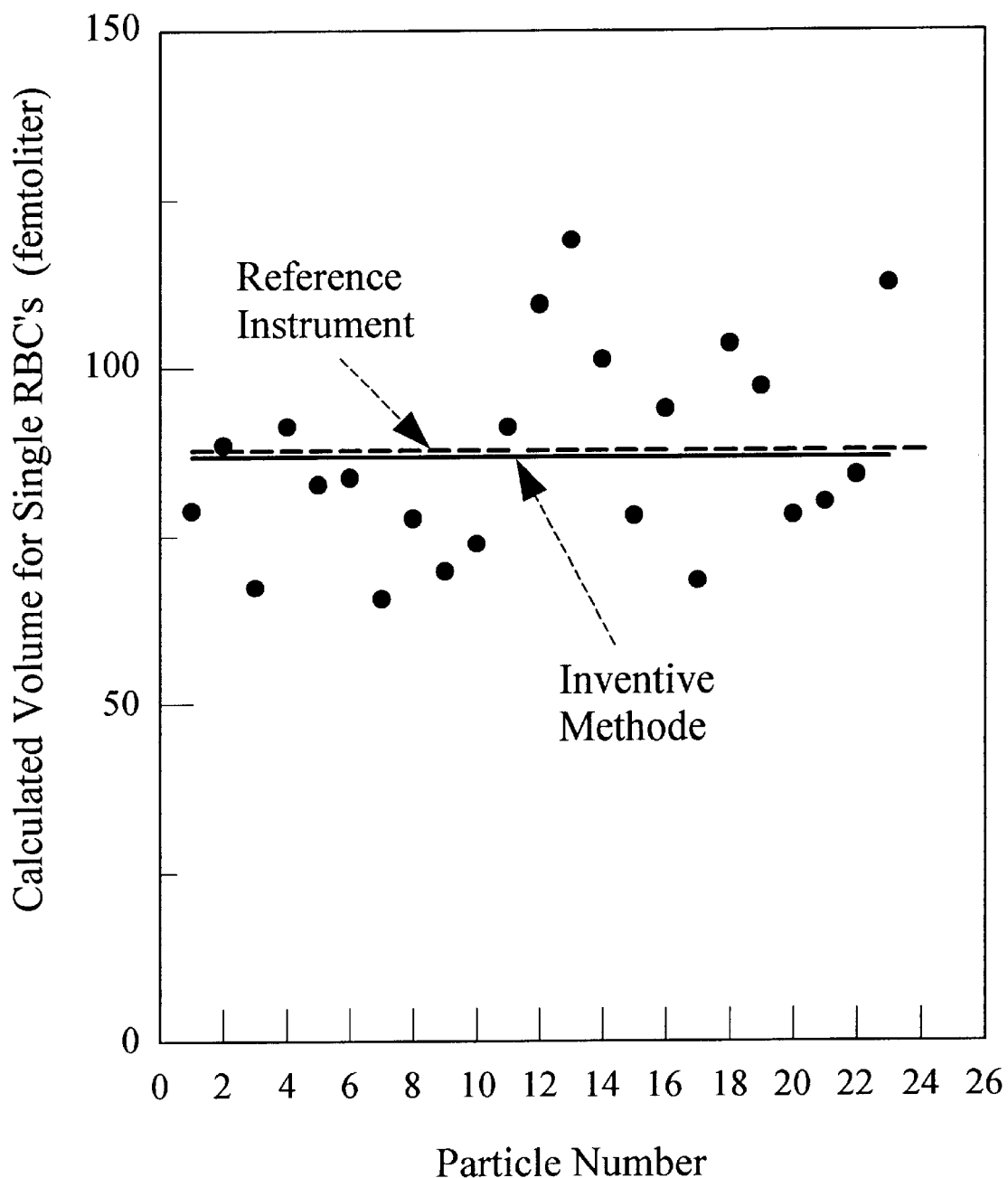
FIG. 4 shows a graphic representation of experimental results, using the present invention, for determining the volume of single red blood cells in whole blood (plotted as calculated volume of single red blood cells versus the particle number.

FIG. 4 shows experimental results in determining the volume of 23 single red blood cells in whole blood, using the method according to the present invention. As an absorbing dye, TO-PRO-3 has been used in a concentration of 2.3 mM/L. The average volume of the population of 23 cells was determined as $V_{avg} = 86.78$ fL (femtoliter). A part of the same blood sample was investigated on a reference instrument (SYSMEX, Inc.) which does not provide the volume for individual cells, but an average value. The average volume as determined by the reference instrument was $V_{ref} = 87.80$ fL. As can be seen from these results, the method according to the present invention provided an average volume for the red blood cells that differed by only 1.17%. The scattering in the volume of the individual cells is as expected.

What is claimed is:

1. A method for determining the volume of particles that are suspended in a liquid sample comprising:
   a) depositing said liquid sample that contains suspended particles into an optical cuvette having an entrance window and an output window at a known distance ($X_0$) from each other;
   b) adding and evenly distributing a light-absorbing dye into the liquid sample that does not leak into the suspended particles;
   c) sending light of such a wavelength through the cuvette that said light is highly absorbed by the added dye, but only weakly absorbed by the suspended particles;
   d) measuring the optical transmission through the cuvette in an area that contains no particles ($I_1/I_0$);
   e) measuring the optical transmission through the cuvette in an area that contains particles ($I_3/I_0'$); and
   f) calculating the volume of the suspended particles based on these transmission values and the known distance of the cuvette windows.

2. The method of claim 1 wherein said light-absorbing dye is a fluorescent dye.

3. The method of claim 1 wherein said light-absorbing dye is TO-PRO-3 or TO-PRO-5.

4. The method of claim 1 wherein said cuvette is a thin cuvette which has a distance between the entrance window and the output window of about 1 micron to about 3000 microns.

5. The method of claim 1 wherein said cuvette is a thick cuvette having a distance between the entrance window and the output window of about 1 micron to about 50 cm.

6. The method of claim 1 wherein said volume is calculated by the equation:

$$V = Ax_0 \left[ 1 - \frac{lg(I_3/I_0')}{lg(I_1/I_0)} \right]$$

wherein $X_0$, $I_3/I_0'$, and $I_1/I_0$ are as defined in claim 1; V is the volume of the particle; A is the area of the particle as determined by an imaging photodetector; and lg is logarithm.

7. The method of claim 1 wherein said liquid sample is blood.

8. The method of claim 7 wherein said cuvette is a thin cuvette which has a distance between the entrance window and the output window of about 1 micron to about 50 microns.

9. The method of claim 7 wherein said cuvette is a thick cuvette having a distance between the entrance window and the output window of about 1 micron to about 50 microns.

10. The method of claim 7 wherein the suspended particles are red blood cells.

11. The method of claim 7 wherein the suspended particles are white blood cells.

12. The method of claim 7 wherein the suspended particles are platelets.

13. A method for determining the volume of particles that are suspended in a liquid sample comprising:
   a) depositing said liquid sample that contains suspended particles into an optical cuvette having an entrance window and an output window;
   b) adding and evenly distributing a light-absorbing dye into the liquid sample that does not leak into the suspended particles;
   c) sending light of such a wavelength through the cuvette that said light is highly absorbed by the added dye, but only weakly absorbed by the suspended particles;
   d) measuring the light intensity ($I_1$) reemerging from the cuvette in an area that contains no particles and where the entrance window and the output window have a first distance from each other;
   e) measuring the light intensity ($I_3$) reemerging from the cuvette in an area that contains a particle and where the entrance window and the output window have said first distance from each other;

f) measuring the light intensity ($I_4$) reemerging from the cuvette in an area that contains no particles and where the entrance window and the output window have a second distance from each other;

g) measuring the light intensity ($I_5$) reemerging from the cuvette in an area that contains no particles and where the entrance window and the output window have a distance from each other that is different from said second distance by a known amount ($\Delta x$);

h) calculating the volume of the suspended particles based on the intensity values ($I_1$, $I_3$, $I_4$, and $I_5$), said known amount of the difference in the distances ($\Delta x$) and the area (A) that is occupied by the particle as determined by an imaging photodetector.

14. The method of claim 13 wherein said light-absorbing dye is a fluorescent dye.

15. The method of claim 13 wherein said light-absorbing dye is TO-PRO-3 or TO-PRO-5.

16. The method of claim 13 wherein said cuvette is a thin cuvette which has a distance between the entrance window and the output window of about 1 micron to about 3000 microns.

17. The method of claim 13 wherein said cuvette is a thick cuvette having a distance between the entrance window and the output window of about 1 micron to about 50 cm.

18. The method of claim 13 wherein said volume is calculated by the equation:

$$V = A \frac{lg(I_1/I_3)}{lg(I_4/I_5)} \Delta_x$$

wherein $I_1$, $I_3$, $I_4$, $I_5$, A and $\Delta x$ are as defined in claim 13; V is the volume of the particle; and lg is logarithm.

19. The method of claim 13 wherein said liquid sample is blood.

20. The method of claim 19 wherein said cuvette is a thin cuvette which has a distance between the entrance window and the output window of about 1 micron to about 50 microns.

21. The method of claim 19 wherein said cuvette is a thick cuvette having a distance between the entrance window and the output window of about 1 micron to about 50 microns.

22. The method of claim 19 wherein the suspended particles are red blood cells.

23. The method of claim 19 wherein the suspended particles are white blood cells.

24. The method of claim 19 wherein the suspended particles are platelets.

* * * * *